United States Patent [19]
Waskönig

[11] Patent Number: 5,389,079
[45] Date of Patent: Feb. 14, 1995

[54] CATHETER UNIT

[76] Inventor: Wilhelm Waskönig, Calle Sacramento, 15, E-04720 Aguadulce (Almeria), Spain

[21] Appl. No.: 110,987
[22] Filed: Aug. 24, 1993
[51] Int. Cl.⁶ .............................................. A61M 5/178
[52] U.S. Cl. .................................... 604/164; 604/264
[58] Field of Search ............... 604/164, 165, 166, 171, 604/264

[56] References Cited

U.S. PATENT DOCUMENTS

| | | | |
|---|---|---|---|
| 3,454,006 | 7/1969 | Langdon | 604/164 |
| 4,209,015 | 6/1980 | Wicks | 604/164 |
| 4,685,904 | 8/1987 | Krebs | 604/164 |
| 5,066,285 | 11/1991 | Hillstead | 604/164 |
| 5,183,470 | 2/1993 | Wettermann | 604/264 |
| 5,215,528 | 6/1993 | Purdy et al. | 604/164 |
| 5,248,298 | 9/1993 | Bedi et al. | 604/264 |
| 5,250,035 | 10/1993 | Smith et al. | 604/164 |

FOREIGN PATENT DOCUMENTS

| | | |
|---|---|---|
| 3218242 | 1/1987 | Germany . |
| 3643235 | 11/1987 | Germany . |
| 8715740 | 3/1988 | Germany . |
| 3918431 | 7/1990 | Germany . |

*Primary Examiner*—John G. Weiss
*Attorney, Agent, or Firm*—Dennison, Meserole, Pollack & Scheiner

[57] ABSTRACT

The catheter unit for continuous spinal anesthesia has inner and outer tubules longitudinal adjustable relative to one another, and a catheter. The inner tubule has a closed point end with a lateral opening. The outer tubule extends along the inner tubule and has an open forward end whose rim is free of cutting edges. When the inner tubule is in position within the body, it can be retracted from the outer tubule to allow longitudinal introduction of the catheter through the outer tube and longitudinally beyond the open forward end.

5 Claims, 3 Drawing Sheets

CATHETER UNIT

BACKGROUND OF THE INVENTION

Small-sized catheters (27 to 32G) are needed in ever-increasing numbers for use, for example, in a continuous spinal anesthesia in the field of regional anesthesia—and not only for anesthesia but also for analgesic purposes.

A catheter unit of the type mentioned can be seen in DE 38 18 431 C1. In this instance the catheter unit consists of a small epidural tube which has an adjustable puncturing element whose point extends beyond the front end of the epidural tube in the interposed position. The tube itself is blunt and without a cutting surface. The puncturing element involves a trocar, which in the interposed position extends beyond the front end of the tube solely with its full point.

Because of the construction of the tube and especially because of its blunt rim, which produces a relatively large cross section, it is essentially impossible to guarantee that the fibers of the dura mater will not be damaged.

A steel tubule for spinal and peridural anesthesia is described in DE 36 43 235 C1. A conical-elliptical tubule has a slope which leads to a lateral opening of the tubule, so as in this way to guide a catheter along the slope through the opening to the outside. Such a design has the disadvantage of making it very difficult for a small-sized, thin-walled catheter to overcome the resistance of the slope. As a result, the catheter has to be equipped with a strong mandrin, which necessarily increases the risk of trauma. It can also be seen that the mandrin can be clamped on the slope in the catheter so that further movement is linked to a simultaneous movement of the tubule. By this means, however, there is still a risk of injury.

A double tubule for peridural anesthesia is known from DE 32 18 242 C2. In this case, the outer tubule is the puncturing tubule and has a sharp, open point.

According to DE 87 15 740 U1, a combination needle for axillary plexus-brachialis anesthesia consists of an inner tubule with a bulgy, cone-shaped stopper which can be soldered, glued or pressed into the tubule.

SUMMARY OF THE INVENTION

The invention involves a catheter unit designed especially for continuous spinal anesthesia and consisting of two tubules (inner and outer) which are relatively adjustable to one another in the longitudinal direction, and the inner tubule consists of a small tube with conical or elliptical, tapered and closed point end with a lateral opening. The outer tubule extends along the inner tubule.

This invention has as its purpose the further development of a catheter unit of the type mentioned so that small-sized catheters can be used without problems, with precise usage of the catheter being possible, and so that it is assured that the longitudinal fibers of the dura mater are not cut but only pushed back when the catheter is inserted, thus essentially excluding the risk of trauma.

The purpose is essentially achieved by having the outer tubule have an opening whose rim has no cutting edges, by having the outer tubule extending proximate the rim area of the lateral opening or directly behind it when the catheter is not in use, by having the inner tubule retractable from the outer tubule when at the desired positioning in a tissue, and by having the catheter exclusively adjustable in the longitudinal direction of the outer tubule.

Through the theory embodied in the invention, the catheter can be inserted into the desired tissue area without rerouting in which case the profile of the inner tubule itself matches the profile of the catheter. In particular, the catheter can penetrate into the spinal region in the longitudinal direction of the tubules without any bending or rerouting being required.

Since a standard conical-elliptical spinal tubule is used, in comparison to the DE 39 18 431 C1 tubule, it has the further advantage of facilitating determination of entry of the spinal tubule needle point into the spinal area as early as possible. The only possible satisfactory way is by seeing the liquid drop out of the needle's hub.

In order to guarantee rigidity and no cutting edge in the outer tubule which forms the guide channel for the catheter so it can be adjusted in its longitudinal direction, the outer tubule preferably is made of a rigid synthetic material such as, for example, TEFLON®. The surrounding tissue exerts a strong contraction on the synthetic outer tubule, but this must, however, resist such pressure in order to be able to make the entire inner diameter of the catheter available.

The rim is micro-rounded so as to ensure no cutting edges. The outer tubule can also have the rim area radially inwardly curved in the direction of the inner tubule. This rim area extends across the top of the lateral opening of the inner tubule. If it is necessary to retract the catheter from the outer tubule still positioned in the patient, these measures make it possible to do so without danger.

In particular then, if the inner tubule has a conical-elliptical point from which the lateral opening extends, the rim of the outer tubule rests against the external wall of the point so that not only are the tissue fibers not damaged, but also so that the spinal tubule can be retracted out of the outer tubule at the same time without any problem and without the outer tubule itself being retracted along with it through static friction or something similar.

In such a case, the rim of the outer tubule can directly overlie the edge of the lateral opening or be slightly behind it.

In order to ensure that the outer and inner tubules form a unit when the catheter unit is inserted, it is recommended that they be joined by means of a Luer-connection.

When the catheter unit of the invention is used for spinal anesthesia, in the case of a positioned spinal tubule whose lateral opening is completely in the spinal area, the opening of the outer tubule by means of which the catheter is inserted into the spinal area will likewise be positioned in the spinal area; however, it will not hurt—and is often even recommended—to simultaneously push the outer tubule about 1 to 2 mm forward when retracting the inner tubule.

The inner tubule should be made of steel. In this case, as mentioned when referring to the outer tubule or the spinal tubule, it can therefore have a traditional conical-elliptical point. The outer tubule can be made of steel. A synthetic material product (for example, TEFLON® or polyurethane) is preferred and has advantages in respect to absolute freedom of cutting edges on the end rim of the outer tubule. This has a positive effect in respect to the nerve fiber bundles in the spinal area, since these should not be damaged.

Further details, advantages and characteristics of the invention can be seen not only from the claims, from the characteristics to be noted in them—by themselves and/or in combination—but also from the following description of the preferred examples to be noted in the drawings.

DESCRIPTION OF THE PREFERRED EMBODIMENTS

Figure 1:
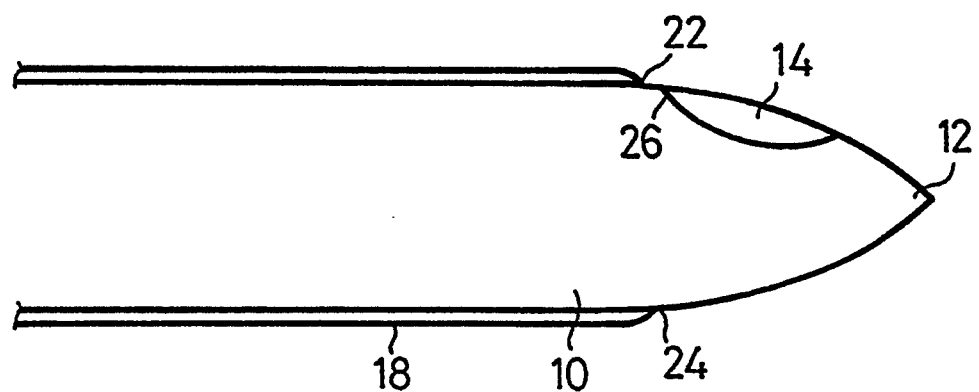
FIG. 1 is a partial schematic view of a spinal tubule encircled by an outer tubule shown in section.
Figure 2:
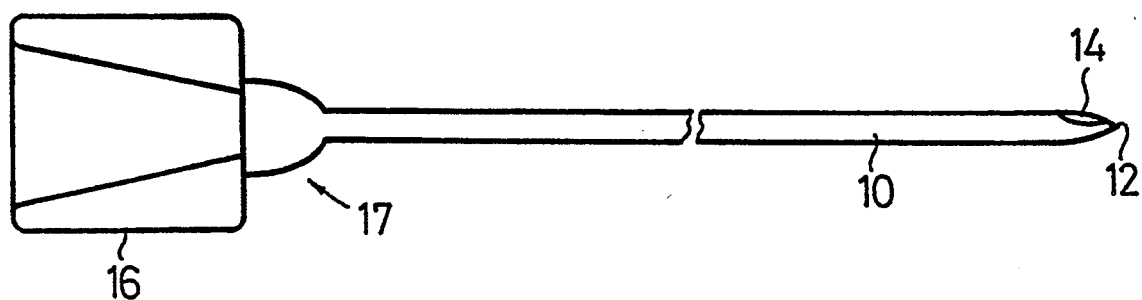
FIG. 2 is a schematic side view of the spinal tubule.

The catheter unit of the invention, which is shown schematically in the figures, includes an inner tubule 10 designed as the spinal tubule with a conical, tapered and closed point 12 with a lateral opening 14. The inner tubule further has a mandrin, not shown, which also fills out the tubule point and seals the lateral opening 14.

The inner or spinal tubule 10 has an attachment 16 preferably made of synthetic material so that it can be attached by means of a so-called Luer-connection to an outer tubule 18 to be positioned over the tubule 10. In this case, the outer tubule 18 has an attachment 20 which also should be made of synthetic material. The area of this attachment, shown in section 21, is the same as that shown in section 17 for attachment 16 of the spinal tubule 10.

Figure 3:
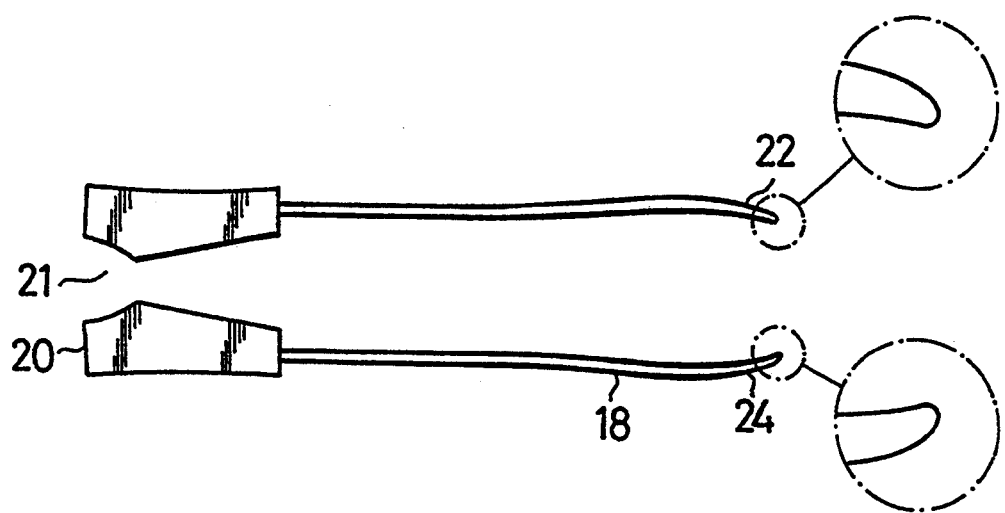
FIG. 3 is a schematic side sectional view of the outer tubule with the rim end radially inwardly curved.
Figure 4:
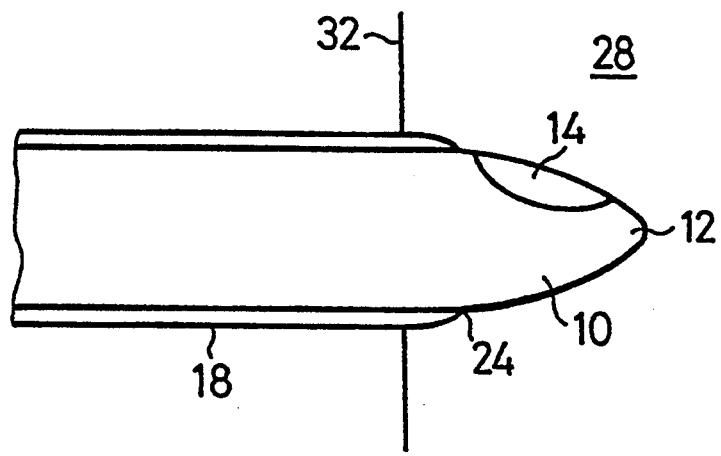
FIG. 4 is a schematic view of the front end of the unit comprised of a spinal tubule and outer tubule, with the point positioned in the spinal area.
Figure 5:
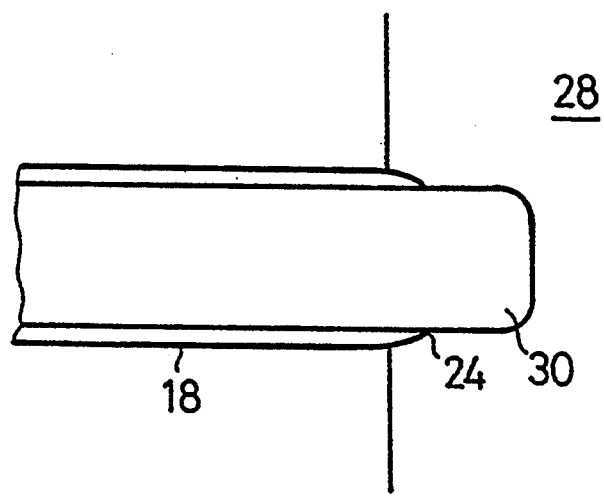
FIG. 5 is a schematic view of the outer tubule with its free end positioned in the spinal area and with a catheter inside it.

The outer tubule 18, which, for example, can have an inner profile of 22 Gauge (G), is micro-rounded in its rim area 22 in such a way that there are no cutting edges. This can be seen in the enlarged representation in FIG. 3. The micro-rounding can be accomplished by thermal forming.

Additionally, if the end 22 should extend into the point area 12, the end area 24 can then be radially bent in the direction of the spinal tubule 10 so that the micro-rounded rim 24 is further "blunted," but without any danger of a crack or opening forming between the rim 22 and the inner tubule 10. This means that the profile of the free rim 22 of the outer tubule 18 matches the profile of the inner tubule 10 to such an extent that in the area of the point 12 the rim 22 rests against the outer wall of the spinal tubule 10. In this instance, the rim 24 preferably runs directly behind the area of the lateral opening, that is, so that, in relation to the point 12 the rim 26 of the lateral opening 14 away from the point 12 is located in front of the rim 22 of the outer tubule 18.

Of course, the rim 22 can align with the proximal portion of rim 26.

Through this construction, in inserting the unit comprised of the inner 10 and outer 18 tubules—which act solely as atraumatic tubules when penetrating into the tissue—it is possible to avoid continuous loss of liquid through tissue damage, so that when penetrating into a spinal area 28, the longitudinal fibers of the dura mater are not cut, but only pushed forward.

Furthermore, the longitudinally large lateral opening 14 avoids interference with or disruption of the atraumatic nature of the point 12 while providing a return liquid flow on the needle attachment which can be seen as quickly as possible, so that there can be an exact determination of the position of the unit made up of the inner and outer atraumatic tubules 10 and 18.

As soon as the desired position of the tubule point 12 within the spinal area 28 is determined, the inner tubule 10 can be retracted in which case it is recommended that the outer tubule 18 be pushed forward 1 to 2 mm, which will ensure that the rim 22 of the outer tubule 18 and therefore also its opening is in the spinal area. After retracting the spinal tubule 10, a catheter 30 can then be inserted through the outer tubule 18 into the spinal area 28, in which case the catheter is moved exclusively in its longitudinal direction.

The Luer-connection for the attachment parts 16 and 20 of the inner and outer tubules 10 and 18 ensures a strong bond, thus ensuring that in penetrating the tissue, particularly the dura mater 32, no pictures of tissue can lodge between the inner 10 and outer 18 tubules.

Since, as already mentioned only the atraumatic point 12 of the inner tubule 10 is visible during penetration into the tissue, the lateral opening 14 being defined longitudinally inward thereof, the tissues of the dura mater are only spread out from one another, without any resulting injury. As soon as the catheter 30 is shoved through the outer tubule 18 and positioned in the spinal area, the outer tubule 18 can be retracted. When this happens, the tissues close tightly around the catheter 30, so that spinal liquid cannot flow out of the spinal area.

I claim:

1. A catheter unit for non-cutting penetration of tissue and the subsequent introduction of a catheter for continuous spinal anesthesia and the like, said unit comprising inner and outer telescoped tubules, said inner tubule being longitudinally removable from said outer tubule and comprising a small tube with a generally conical end portion continuously tapering along generally elliptical arcs to and terminating in a closed distal point, a lateral opening defined through said tapered end portion longitudinally inward of said distal point, said opening having a proximal rim portion, said outer tubule having an open forward end defined by a non-cutting rim positioned proximate the proximal rim portion of the opening for non-cutting insertion of said telescoped tubules, said inner tubule being proximally removable from said outer tubule when at the desired positioning in tissue, whereby said outer tubule is adapted to receive a catheter longitudinally therethrough and longitudinally beyond said outer tubule open forward end subsequent to removal of said inner tubule.

2. A catheter unit in accord with claim 1 wherein said rim of said outer tubule is micro-rounded.

3. A catheter unit in accord with claim 1 wherein said outer tubule rim is radially inwardly curved toward said inner tubule.

4. A catheter unit in accord with claim 1 wherein said rim of said outer tubule engages against said end portion peripherally thereabout.

5. A catheter unit in accord with claim 1 wherein said outer tubule is made of synthetic material, said outer tubule rim being micro-rounded and thermal formed.

* * * * *